(12) United States Patent
Johnson (10) Patent No.: US 11,772,097 B2
(45) Date of Patent: Oct. 3, 2023

(54) SIMULTANEOUS SPOT TEST AND STORAGE OF BLOOD SAMPLES (71) Applicant: RENEGADEXBIO, PBC, Berkeley, CA (US)

(72) Inventor: Brandon T. Johnson, Cambridge, MA (US)

(73) Assignee: RENEGADEXBIO, PBC, Berkeley, CA (US)

( * ) Notice: Subject to any disclaimer, the term of this patent is extended or adjusted under 35 U.S.C. 154(b) by 74 days.

(21) Appl. No.: 16/657,041

(22) Filed: Oct. 18, 2019

(65) Prior Publication Data
US 2020/0206743 A1    Jul. 2, 2020

Related U.S. Application Data (63) Continuation-in-part of application No. 16/164,988, filed on Oct. 19, 2018, now Pat. No. 11,358,138.

(60) Provisional application No. 62/772,135, filed on Nov. 28, 2018.

(51) Int. Cl.
| | |
|---|---|
| *G01N 33/53* | (2006.01) |
| *B01L 99/00* | (2010.01) |
| *B01L 3/00* | (2006.01) |
| *G01N 33/566* | (2006.01) |
| *B01L 3/02* | (2006.01) |

(52) U.S. Cl.
CPC ........ *B01L 3/502792* (2013.01); *B01L 3/022* (2013.01); *B01L 3/50857* (2013.01); *G01N 33/566* (2013.01); *B01L 2300/0825* (2013.01); *B01L 2300/0829* (2013.01); *B01L 2300/0832* (2013.01)

(58) Field of Classification Search
None
See application file for complete search history.

(56) References Cited

U.S. PATENT DOCUMENTS

| | | |
|---|---|---|
| 3,430,813 A | 3/1969 | Gilmont et al. |
| 3,767,085 A | 10/1973 | Cannon et al. |
| 4,185,628 A | 1/1980 | Kopfer |
| 4,257,267 A | 3/1981 | Parsons |
| 4,386,606 A | 6/1983 | Tretinyak et al. |
| D284,214 S | 6/1986 | Hatcher et al. |

(Continued)

FOREIGN PATENT DOCUMENTS

| | | |
|---|---|---|
| EP | 2772306 A1 | 9/2014 |
| EP | 3088083 B1 | 8/2018 |

(Continued)

OTHER PUBLICATIONS

International Search Report and Written Opinion dated Jan. 27, 2020 for Related PCT/US19/56918.

(Continued)

*Primary Examiner* — Paul S Hyun
(74) *Attorney, Agent, or Firm* — Sidharth Kapoor; Nina Habib Borders; Reed Smith LLP (57) ABSTRACT

A blood sample collection and/or storage device includes a two-piece housing that encompasses a port at which a fingertip blood sample is collected. After the sample is taken, the two-piece housing is moved to a closed position to protect the sample for storage and optionally process the sample within the housing. The housing may also be opened to access the stored sample for further processing.

15 Claims, 6 Drawing Sheets

(56) References Cited

U.S. PATENT DOCUMENTS

| | | | |
|---|---|---|---|
| 4,690,005 A | 9/1987 | Tervamaki et al. | |
| 4,915,695 A | 4/1990 | Koobs | |
| 5,013,667 A | 5/1991 | Lynn et al. | |
| D324,426 S | 3/1992 | Fan et al. | |
| D331,807 S | 12/1992 | Sodergren | |
| 5,339,830 A | 8/1994 | Blake, III | |
| 5,384,264 A | 1/1995 | Chen et al. | |
| 5,518,006 A | 5/1996 | Mawhirt et al. | |
| D410,287 S | 5/1999 | Von Boetticher | |
| D411,621 S | 6/1999 | Eisenbarth et al. | |
| 6,093,156 A | 7/2000 | Cunningham et al. | |
| 6,106,779 A | 8/2000 | Buechler et al. | |
| 6,120,733 A | 9/2000 | Goodman et al. | |
| 6,372,514 B1 | 4/2002 | Lee | |
| 6,399,398 B1 | 6/2002 | Cunningham et al. | |
| 6,524,864 B2 | 2/2003 | Fernandez Decastro | |
| D512,512 S | 12/2005 | Bell et al. | |
| 7,435,237 B2 | 10/2008 | Tan | |
| D590,063 S | 4/2009 | Garthoff et al. | |
| 7,803,319 B2 | 9/2010 | Yang et al. | |
| 7,838,258 B2 | 11/2010 | Yang et al. | |
| D631,556 S | 1/2011 | Shi et al. | |
| 8,105,554 B2 | 1/2012 | Kanigan et al. | |
| 8,173,380 B2 | 5/2012 | Yang et al. | |
| 8,206,650 B2 | 6/2012 | Samsoondar | |
| 8,329,119 B2 | 12/2012 | Pearcy et al. | |
| D676,145 S | 2/2013 | Kouge et al. | |
| 8,561,795 B2 | 10/2013 | Schott | |
| 8,741,230 B2 | 6/2014 | Holmes et al. | |
| 8,808,202 B2 | 8/2014 | Brancazio | |
| 8,821,412 B2 | 9/2014 | Gonzalez-Zugasti et al. | |
| 8,827,971 B2 | 9/2014 | Gonzalez-Zugasti et al. | |
| 8,940,539 B2 | 1/2015 | Pearcy et al. | |
| 8,976,983 B2 | 3/2015 | Jang et al. | |
| D728,818 S | 5/2015 | Burroughs et al. | |
| 9,023,292 B2 | 5/2015 | Rostaing et al. | |
| 9,033,898 B2 | 5/2015 | Chickering, III et al. | |
| 9,040,236 B2 | 5/2015 | Hill et al. | |
| 9,041,541 B2 | 5/2015 | Levinson et al. | |
| D733,313 S | 6/2015 | Kouge et al. | |
| D734,482 S | 7/2015 | Peterman et al. | |
| 9,113,836 B2 | 8/2015 | Bernstein et al. | |
| 9,119,578 B2 | 9/2015 | Haghgooie et al. | |
| 9,176,126 B2 | 11/2015 | Holmes et al. | |
| 9,289,763 B2 | 3/2016 | Berthier et al. | |
| 9,295,417 B2 | 3/2016 | Haghgooie et al. | |
| 9,386,948 B2 | 7/2016 | Holmes et al. | |
| 9,427,184 B2 | 8/2016 | Holmes et al. | |
| 9,636,062 B2 | 5/2017 | Holmes et al. | |
| 9,987,629 B2 | 6/2018 | Berthier et al. | |
| D822,225 S | 7/2018 | Moon et al. | |
| D824,530 S | 7/2018 | Velschow et al. | |
| 10,180,421 B2 * | 1/2019 | Johnson | A61B 5/15003 |
| D855,210 S | 7/2019 | Ito et al. | |
| D861,189 S | 9/2019 | Lampropoulos et al. | |
| D861,915 S | 10/2019 | Zakrys et al. | |
| 10,488,424 B2 | 11/2019 | Steckl et al. | |
| 10,545,140 B2 | 1/2020 | Cheng et al. | |
| 10,597,651 B2 | 3/2020 | Pottathil | |
| D894,422 S | 8/2020 | Johnson | |
| D895,140 S | 9/2020 | Heron | |
| D895,146 S | 9/2020 | Osmus et al. | |
| 11,358,139 B2 * | 6/2022 | Johnson | A61B 5/150755 |
| 2002/0031839 A1 * | 3/2002 | Mcneirney | G01N 33/54386 436/518 |
| 2002/0173047 A1 | 11/2002 | Hudak et al. | |
| 2003/0235825 A1 | 12/2003 | Shea et al. | |
| 2005/0119589 A1 | 6/2005 | Tung et al. | |
| 2005/0232813 A1 | 10/2005 | Karmali | |
| 2006/0228259 A1 | 10/2006 | Samsoondar | |
| 2007/0184547 A1 | 8/2007 | Handique et al. | |
| 2008/0025872 A1 | 1/2008 | Dykes et al. | |
| 2008/0145835 A1 | 6/2008 | Alajem et al. | |
| 2009/0117665 A1 | 5/2009 | Tung et al. | |
| 2010/0099112 A1 | 4/2010 | Zhou et al. | |
| 2010/0210970 A1 | 8/2010 | Horikawa et al. | |
| 2010/0222703 A1 | 9/2010 | Takashima et al. | |
| 2011/0124984 A1 | 5/2011 | Rostaing | |
| 2011/0127294 A1 | 6/2011 | Pearcy et al. | |
| 2011/0152720 A1 | 6/2011 | Zappia et al. | |
| 2011/0212453 A1 | 9/2011 | Agarwal et al. | |
| 2012/0029830 A1 * | 2/2012 | Turner | A61B 5/15113 702/19 |
| 2012/0168305 A1 | 7/2012 | Hunter | |
| 2013/0171044 A1 | 7/2013 | Nikonorov et al. | |
| 2013/0172698 A1 | 7/2013 | Reynolds et al. | |
| 2013/0211289 A1 | 8/2013 | Moga et al. | |
| 2013/0247694 A1 | 9/2013 | Chen et al. | |
| 2013/0280725 A1 | 10/2013 | Ismagilov et al. | |
| 2013/0309136 A1 * | 11/2013 | Johnson | G01N 1/38 422/522 |
| 2013/0309679 A1 | 11/2013 | Ismagilov et al. | |
| 2014/0050620 A1 | 2/2014 | Johnson et al. | |
| 2014/0073990 A1 | 3/2014 | Holmes et al. | |
| 2014/0303518 A1 | 10/2014 | Pierce et al. | |
| 2014/0323911 A1 | 10/2014 | Sloan et al. | |
| 2014/0329258 A1 | 11/2014 | Fleming | |
| 2015/0069072 A1 | 3/2015 | Kelley et al. | |
| 2015/0231627 A1 | 8/2015 | Sloan et al. | |
| 2015/0273467 A1 | 10/2015 | Sloan et al. | |
| 2015/0346105 A1 | 12/2015 | Gutsell et al. | |
| 2016/0051981 A1 | 2/2016 | Berthier et al. | |
| 2016/0349156 A9 | 12/2016 | Menon et al. | |
| 2017/0023546 A1 | 1/2017 | Holmes et al. | |
| 2017/0042460 A1 | 2/2017 | Holmes et al. | |
| 2017/0108477 A1 | 4/2017 | Ozbal | |
| 2017/0176306 A1 | 6/2017 | Boehm et al. | |
| 2017/0227536 A1 | 8/2017 | Matsuura | |
| 2018/0356393 A1 | 12/2018 | Piasio et al. | |
| 2019/0111421 A1 | 4/2019 | Johnson | |
| 2019/0126266 A1 | 5/2019 | Johnson | |
| 2019/0381499 A1 | 12/2019 | Johnson | |
| 2020/0121234 A1 | 4/2020 | Johnson | |

FOREIGN PATENT DOCUMENTS

| | | |
|---|---|---|
| WO | 2017075050 A1 | 5/2010 |
| WO | WO-2012003306 A1 | 1/2012 |
| WO | WO-2017123668 A1 | 7/2017 |

OTHER PUBLICATIONS

1/1-Designs Questel. APN—3020160043209 (2019.).

A new era for blood collection and testing. Online, published date unkown. Retrieved on Nov. 18, 2019 from URL https://www.bostonmicrofluidics.com/.

Buckle. Online, published date Jun. 5, 2016. Retrieved on Nov. 22, 2019 from URL: http://www.8472.co.uk/misc_buckles_double.htm.

Garden House/Joaqufn Alvado Banon. Online, published date 2012. Retrieved on Nov. 22, 2019 from URL: https://www.archdaily.com/306750/garden-house-joaquin-alvado-banon.

PCT/US2018/056629 International Search Report and Written Opinion dated Jan. 22, 2019.

PCT/US2019/033878 International Search Report and Written Opinion dated Aug. 20, 2019.

PCT/US2019/033879 International Search Report and Written Opinion dated Oct. 25, 2019.

PCT/US2019/056926 International Search Report and Written Opinion dated Jan. 24, 2020.

PCT/US2019/056930 International Search Report and Written Opinion dated Jan. 9, 2020.

PCT/US2020/049460 International Search Report and Written Opinion dated Feb. 19, 2021.

Syringe Selection Guide, Complete Guide to Selecting the Right Hamilton Microliter, Gastight, and Specialty Syringes for your Application. Hamilton: 1-24 (2017).

Through the isosceles trapezoid window. Online, published date Dec. 6, 2006. Retrieved on Nov. 22, 2019 from URL: https://www.flickr.com/photos/page94/315753467.

(56) References Cited

OTHER PUBLICATIONS

U.S. Appl. No. 16/164,988 Final Office Action dated Dec. 29, 2021.
U.S. Appl. No. 16/777,959 Non-Final Office Action dated Feb. 4, 2021.
U.S. Appl. No. 16/777,959 Final Office Action dated Aug. 10, 2021.
U.S. Appl. No. 16/657,101 Non-Final Office Action dated Oct. 6, 2021.
U.S. Appl. No. 16/421,619 Non-Final Office Action dated Aug. 13, 2021.
U.S. Appl. No. 16/421,619 Final Office Action dated Jan. 14, 2022.
U.S. Appl. No. 16/242,084 Non-Final Office Action dated Jul. 16, 2021.
U.S. Appl. No. 16/242,084 Final Office Action dated Jan. 11, 2022.
U.S. Appl. No. 16/16/,623 Non-Final Office Action dated Oct. 22, 2021.
U.S. Appl. No. 16/164,988 Non-Final Office Action dated Jul. 20, 2021.
Extended European Search Report issued in European Patent Application No. 18869777.5 dated Jul. 1, 2021.

* cited by examiner

SIMULTANEOUS SPOT TEST AND STORAGE OF BLOOD SAMPLES

CROSS REFERENCE TO RELATED APPLICATIONS

This application claims priority to U.S. Provisional Patent Application entitled "Simultaneous Spot Test and Storage of Blood Samples", Ser. No. 62/772,135 filed Nov. 11, 2018. It also relates to U.S. Patent Application entitled "Fluid Sample Collection Device", Ser. No. 16/164,988 filed Oct. 19, 2018. The entire contents of those applications are hereby incorporated by reference.

BACKGROUND

Technical Field

This patent application relates to devices and methods for body fluid sample collection.

Background Information

Blood used for diagnostic testing is most often extracted from a patient with a hypodermic needle and collected in a test tube. The collected blood is then packaged for shipment to a remote lab where various diagnostic tests are performed. However, many diagnostic tests require significantly less volume than the actual collected sample. Separation of cellular components from the sample is also needed for some tests.

Many tests only require small blood samples, where a finger stick rather than a hypodermic needle can produce enough blood. But this small amount of blood cannot be easily transported to a remote lab. If the testing method cannot be immediately used at the same time the blood is extracted, convenient and reliable methods of collecting, prepping, and preserving small amounts of blood are still needed.

US Patent Publication US 2014/0050620A1, assigned to Boston Microfluidics, Inc., describes several ways to implement a portable, user-friendly device for collecting a biological fluid sample and stabilizing it for transport to a remote lab. The devices include a small, hand-held housing that provides a chamber for collecting a fluid sample. Movement of the housing itself, and/or mechanisms located within the housing, initiate collection of a predetermined, metered volume of a fluid sample. The devices may also stabilize the collected sample and/or seal the sample in the chamber. Other mechanisms in the device may mix the collected sample with a reagent.

SUMMARY

A sample collection device can be used to collect, meter, analyze and/or store a body fluid sample such as a blood sample. Fluid collected from a patient is first introduced into the device via a sample port, such as by directing blood droplets from a fingertip into a well, or in other ways. In some configurations, capillaries or other microfluidic channels then extract a metered amount of blood from the sample port and deposit it onto a media via capillary action. One or more plungers may further provide mechanical force to encourage dispensing fluid from the metering capillaries and onto the media.

In a preferred arrangement, the media includes two or more membranes, immunoassay strips, or other substrates. For example, the media may include both a collection membrane and an immunoassay strip. The collection membrane(s) and immunoassay strip(s) may be disposed parallel to one another, adjacent an outlet of the capillaries. The collection membrane(s) may receive and store a blood sample from some capillaries, and the immunoassay (or other test) strip(s) may receive and process a blood sample provided from other capillaries. Types of membranes such as those based on plastic or glass, or microfluidic detectors may be used.

In some configurations, the sample is delivered to an assay region within the housing where captured blood molecules are exposed to a surface that binds to analytes. These analytes can then be bound by a conjugate to make them detectable. For example, the bound analytes may also modify the optical or electrical properties of the surface they are bound to, making them directly detectable via visual inspection, or electronic circuits.

Having the ability to perform different processes in parallel on the same blood sample provides several advantages. For example, one membrane may have an analyte that provides immediate results for a critical condition (such as HIV or hepatitis C), and another membrane may be a collection media, such as LF-1 paper, designed store the blood sample for testing of less critical conditions, at a later time in a lab (such as testing for glucose).

In some configurations, the plungers may be attached to one or more movable housing pieces, such that when the housing is moved from an open to a closed position, the capillaries are exposed to the blood in the sample port.

Some embodiments of the device include a stabilization or anticoagulation agent arranged to engage the fluid as it is dispensed onto the media. The agent may be heparin and/or EDTA. The stabilization agent may be coated or deposited onto an interior of at least one of the capillaries, or the plungers, or the media. This configuration may also include a desiccant located adjacent or on the media.

In other arrangements, an assay region may also be located between the capillaries and the media, such that a stored reagent is mixed with the fluid when the fluid is dispensed, e.g., as the housing is moved from the open position to the closed position.

The housing may also include one or more windows positioned in a location such that at least a portion of the capillaries and/or media are visible through the window. It may be desirable to have a window to view each of the two or more media. However, in other configurations, at least some of the media may be hidden from view when the housing is closed. One practical use for this may be when the device collects blood for use in clinical trials, such as a United States' Food and Drug Administration (FDA) 501(k) substantial equivalency test.

The media may take different forms. For example, it may include a mylar substrate having a pair of engagement tabs spaced apart from one another. The media is then disposed on the substrate and held in place between the engagement tabs.

A backbone may be included within the housing to support the two or more media and hold then in place adjacent the capillary exit ports.

DETAILED DESCRIPTION OF PREFERRED EMBODIMENTS

Figure 1:
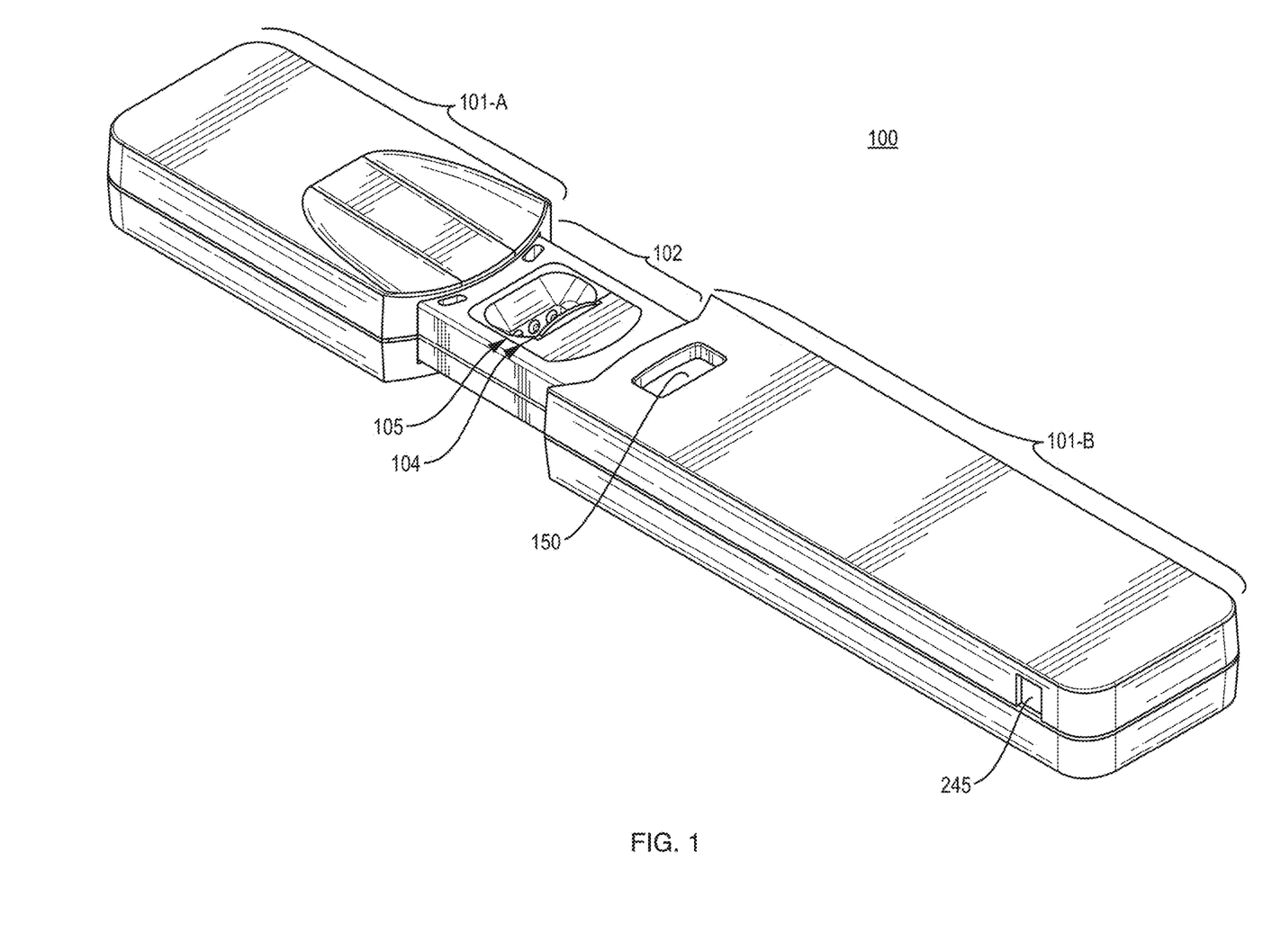
FIG. 1 is an isometric view of a blood sample collection device in the open position, before it is used.

FIG. 1 is an isometric view of an example fluid collection device 100. The device 100 includes a two-piece housing 101 that supports and encloses a fluid sample port 102. The housing 101 includes a first housing piece 101-A and second housing piece 101-B. In this view, the housing is in the open position with the two housing pieces 101-A, 101-B spaced apart from one another, to provide access to the sample port 102. A sample collection well 104 and one or more capillaries 105 located adjacent the sample port 102 are partially visible in this figure. A window 150 in the housing permits a user to confirm the status of one or more portions of a fluid sample in the process of being collected and/or stored within the device 100.

Figure 2:
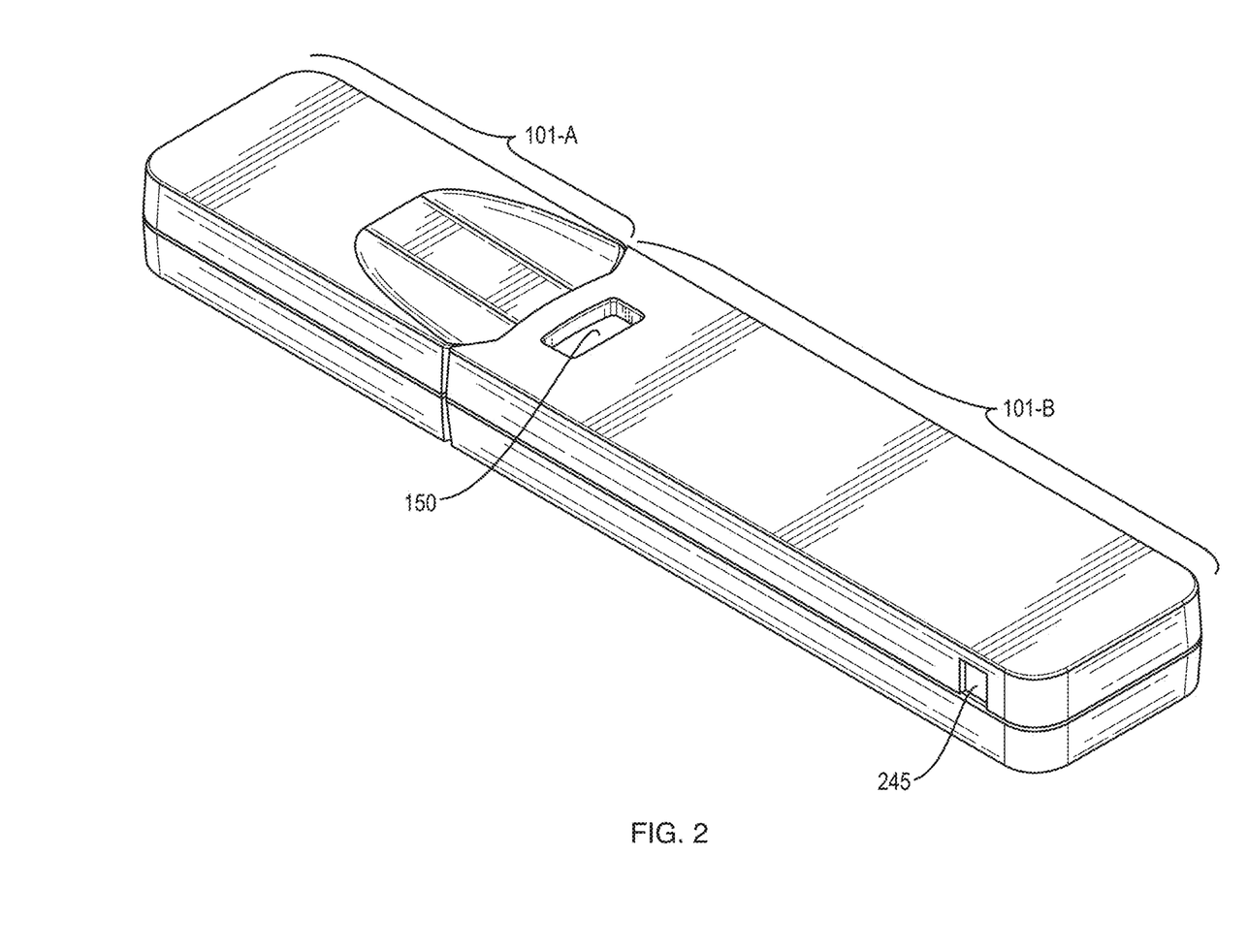
FIG. 2 is a view of the collection device in the closed position.

FIG. 2 is a similar isometric view of the device 100. In this view, a blood sample has been taken via the sample port 102, and the two housing pieces 101-A and 101-B have been pushed together to place the device 100 in a closed position. In this closed position, the window 150 still provides access to the blood collection status.

The device 100 is typically used to collect a blood sample as follows. The device 100 is initially presented in its open position, as per FIG. 1, to provide access to the well 104. A user, such as a patient herself or a health care professional, then uses a lancet to produce a blood sample such as from a finger tip. Drops of whole blood are then taken with the finger positioned near to, above, adjacent to, or even in contact with the well 104 or other parts of the sample port 102 to minimize blood spillage.

Blood is then eventually drawn into the rest of the device 100 in one or more different ways. As will be explained in more detail below for one embodiment, blood flows and/or is first drawn from the well 104 by one or more collection capillaries 105 adjacent the sample port via capillary action. The capillaries may be visibly transparent so that the user can confirm that blood is being properly drawn into the device 100. The capillaries 105 can optionally be pre-coated with reagents such as heparin and/or EDTA for subsequent stabilization and preservation of the sample. The capillaries 105 can also have a known and predetermined volume, in which case the incoming sample is precisely metered. The collection capillaries 105 then direct the metered sample to a media inside the device housing 101

The user, who can be the patient himself/herself or a healthcare professional, then manually closes the device 100 by pushing the two housing pieces 101-A, 101-B together, resulting in the housing position shown in FIG. 2. As more fully explained below, the motion associated with closing the housing may then optionally enact one or more mechanisms that further process the sample, and to securely store it inside the device 100.

The window 150 may include a transparent piece of material that enables the user to view the state of the sample port 102, the well 104, and/or collection capillaries 105. In that way, an indication of whether a sufficient sample of blood is being drawn into the device 100 (when the housing 101 is in the open position of FIG. 1) or was drawn into the device (when the housing 101 is in the closed position as in FIG. 2).

Figure 3A:
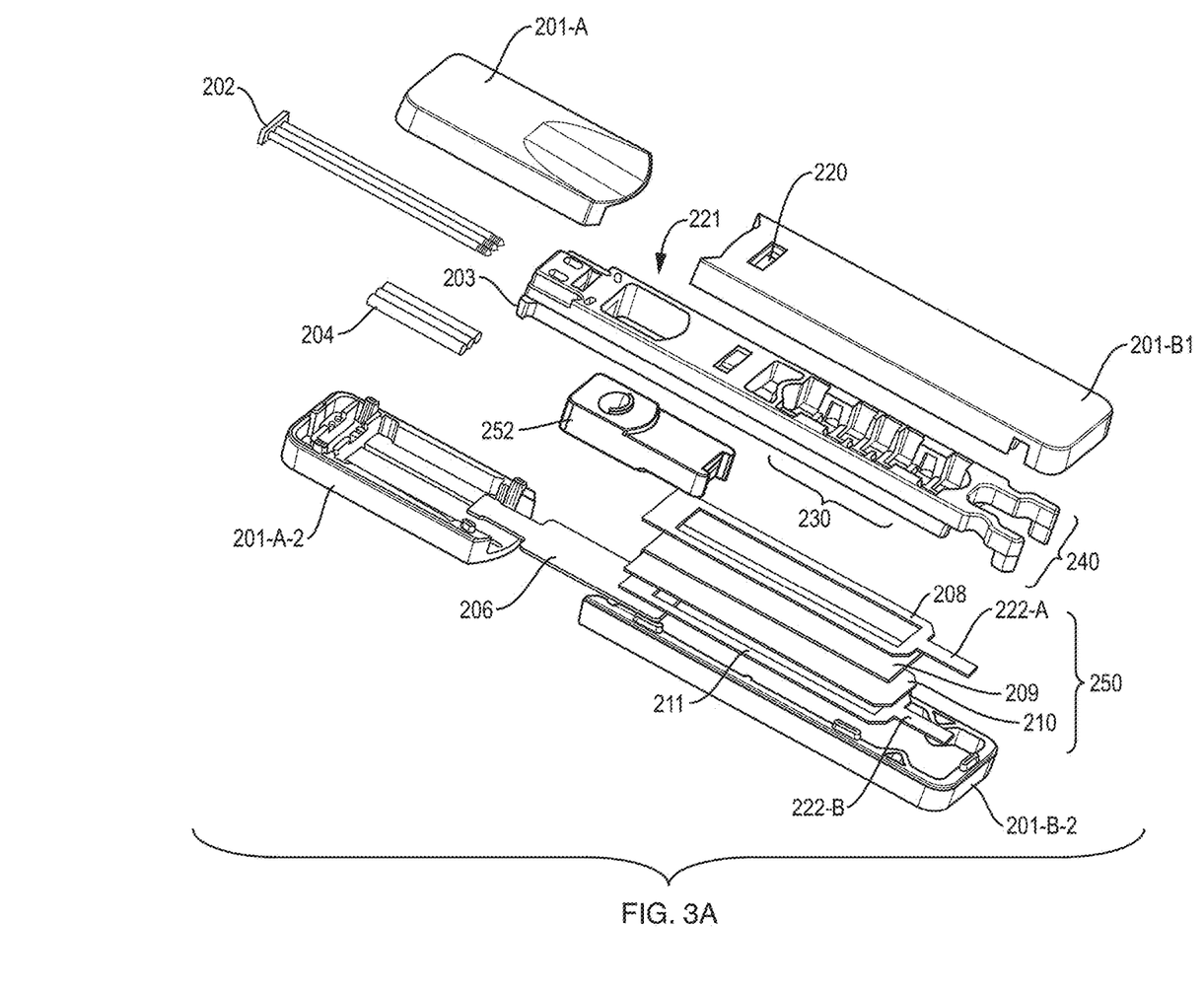
FIG. 3A is an exploded view showing components of a collection device having a single media.

FIG. 3A is a more detailed, exploded view of the components of an example device 100. The first housing piece 101-A consists of a top case 201-A-1 and bottom case 201-A-2, and second housing piece 101-B consists of a top case 201-B-1 and bottom case 201-B-2.

A backbone structure 203 provides a support for the two housing pieces 101-A, 101-B. The inside vertical walls of the housing pieces 201-A, 201-B may engage elongated slots or other structures formed in the backbone 203, thus enabling at least second housing piece 101-B to slide back and forth along the backbone, and to thus move the housing into the open or closed position. In one arrangement, first housing piece 101-A remains fixed in position on backbone 203. However other embodiments are possible where first housing piece 101-A slides on backbone 203 and second housing piece 101-B remains fixed, or where both housing pieces 101-A, 101-B can slide with respect to one another.

The backbone 203 also supports other components of the device 100. For example, the backbone 203 provides a location for the sample collection port 102, as formed from an inlay part (also referred to as a capillary support element) 252. A plunger rack 202 is also supported by the backbone 203. The backbone 203 may further include a ribbed section 230 to support a desiccant tablet (not shown in FIG. 3) to further dry the collected sample. The backbone 203 may also have tines at an end that provide a ratcheting closure 240, which is activated when the two housing pieces 101-A, 101-B are pushed together.

Capillaries 204 (also referred to with reference number 105 in other figures) are inserted into and held in place by longitudinal holes (not shown in FIG. 3) formed in the inlay 252. The capillaries and may be formed as a rigid tube of precisely defined volume, in which case they also serve a metering function. The capillaries 204 extract a defined quantity of blood by engagement with the blood in the sample collection port 102 through capillary action. The inlay 252 may fit into a hole 221 in backbone 203. As explained in further detail below, the inlay 252 defines the location of a well 104 into which the patient's blood is introduced.

The capillaries 204 can optionally be pre-coated with reagents, heparin, EDTA, or other substances.

One or more capillaries 204 may also store a predetermined amount of a liquid reagent. Such a reagent may then be dispensed together or in parallel with the blood sample when the housing is moved from the open to the closed position. However, reagents of other types may also be located in a storage region within the housing. The storage region (not designated in the figures), may hold a first type of reagent such as a solid surface or substrate, and a second type being a liquid storage chamber, each of which are placed in the path of the blood sample collected by the device 100.

In one arrangement, the one or more plungers 202 firmly engage with the inner diameter of the capillaries 204, creating a shutoff that blocks off any excess blood sample while also pushing the metered sample volume to the subsequent downstream processing steps.

A base 206 may also fit into the backbone 203 to provide additional mechanical support for a blood collection element 250. The collection element 250 may consist of a sample media (also called a membrane herein) 209 that is supported and/or held in place by other components that assist with handling the sample media 209 when it is removed from the device 101 for processing by a laboratory. These other parts of the collection element 250 may include the base 206, a top frame 208, media support 210, and bottom frame 211. The top 208 and bottom 211 frame may have extensions 222-A, 222-B on an outboard end. The extensions 222 further assist with handling the collection element 250 during and after its removal from the housing 101.

Figure 3B:
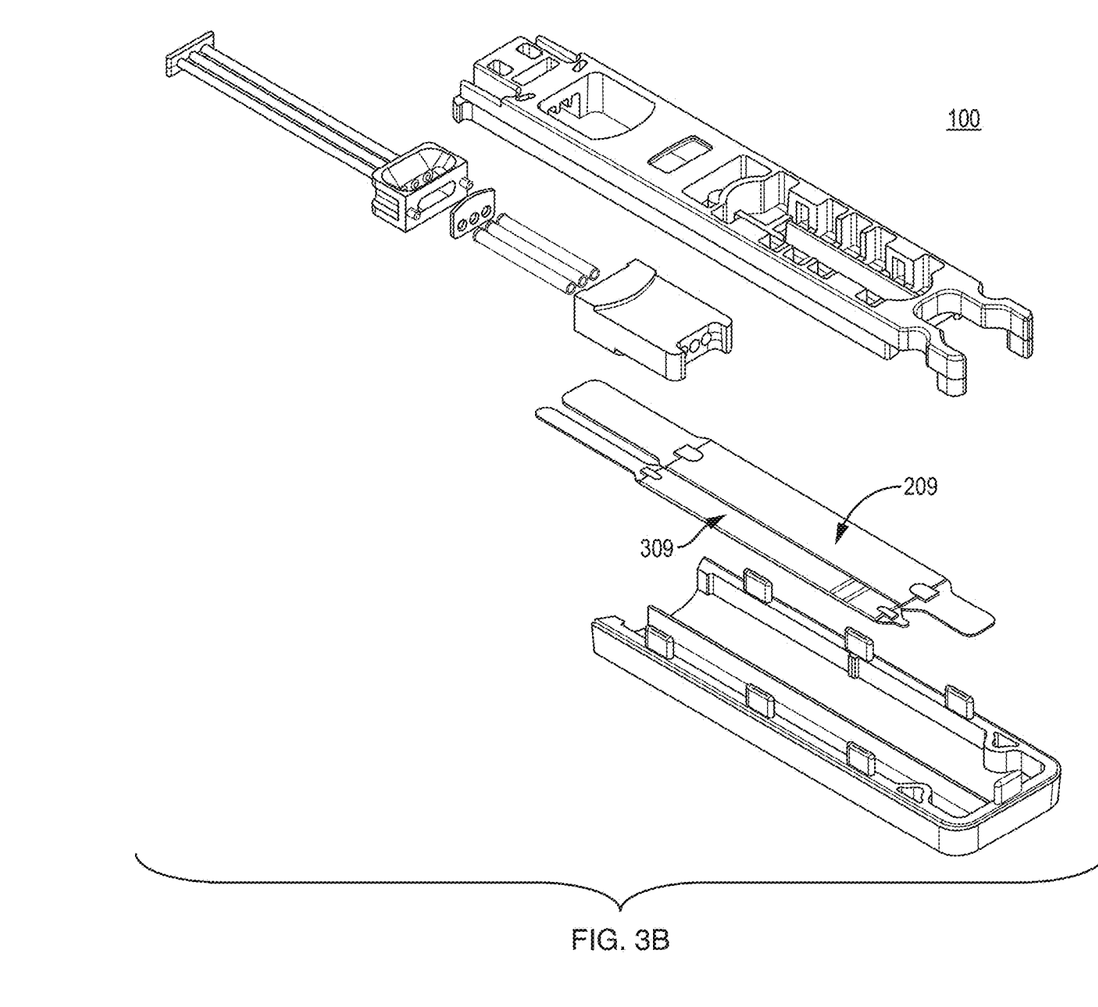
FIG. 3B is an exploded view of another example device having multiple media, such as a storage membrane and an immunoassay strip.

FIG. 3B is an exploded view of another example device 100, similar to the device in FIG. 3A. However, this device 100 presents the blood sample to two types of media, including both a collection membrane 209 and an immunoassay strip 309. The membrane 209 and strip 309 may be arranged in parallel. The collection membrane 209 receives and stores a blood sample from some capillaries, and the immunoassay (or other test) strip 309 may receive and process a blood sample from other capillaries.

Other arrangements for two or more types of media are possible. For example, a collection membrane 209 and immunoassay strip 309 may be stacked on top of one another (instead of located in parallel with one another). It may be desirable for the test strip to be visible but the collection strip to not be visible, or vice versa. In some arrangements, a flow thorough test in addition to a lateral flow test may be housed in the same device. In addition to testing, a multiple layer (flow path) configuration could be used for sample separation (e.g., red blood cells on one layer, plasma on another) or for isolating competing analytes.

Samples from a first set of the capillaries may be exposed to an anti-coagulant such as heparin and directed to a sample storage media such as the membranes described herein. Samples from a second set of the capillaries may be mixed with reagent and directed for an on-the-spot test (e.g., via chemical media or electronic sensors) that provide an immediate test indication (such as via a color change in a chemical media or via a display of an electronic sensor output).

In one example use case, a single device provides and on-the-spot test for an immediate indication of a serious condition such as HIV or hepatitis C. The same device collects and stores a blood sample at the same time, which can then be used for less critical tests at a remote lab, such as blood glucose.

Other test strips may include colored bands that indicate a result of a test performed within the device itself. For example, test strips may be configured to indicate an HIV or hepatitis C condition. In the case of testing for HIV, the strip may be a nitrocellulose film that includes a detection area coated with HIV recombinant antigens and a control area. Qualitative test strips for the presence of the hepatitis C virus in whole blood and plasma can also be applied.

The media 209 may be a plasma separation membrane or filter of various types located at or near an exit port of the capillaries 105. For example, the membrane may be a mixed-cellulose ester membrane such as the Pall Vivid Plasma Separation membrane available from Pall™ Corporation. The membrane 209 may also be an LF1 glass fiber membrane (sold by General Electric™ Company) or some other media designed to receive serum or whole blood which it then separates into a blood portion and a plasma portion. A media such as LF1 paper has a fibrous structure that causes differential migration of the sample, with a slower rate for red cells, resulting in a gradual separation of plasma sample as it migrates down the paper. The membrane 209 can optionally be previously impregnated with heparin, EDTA, sugars, or other stabilization agents. LF1 paper, which separates plasma from red blood cells through a fiber matrix, is preferred in some embodiments, because it causes a slower migration rate for the blood cells. However other types of separation membranes for blood either liquid or dried may be used.

Plasma separation may also be achieved through non-membrane microstructures that exclude red cells by size. For example, plasma separation can be achieved or enhanced by selectively binding red cells as well. Binding agents are typically coated on a membrane or micro structure but could also be deposited in a channel.

The sample media can also be coated with various chemicals to perform a test, such as an assay, on the collected sample. Thus, an immunoassay strip 309 can be substituted for all, or for part of, or together with the sample media 209. When device 100 is closed, the sample is delivered to a sample pad area on the immunoassay strip.

The media itself may be the aforementioned cellulose or glass fiber media, or other porous or non-porous media such as a plastic or glass. The media may include microfluidics chip(s).

The window 150 permits visual confirmation that the blood sample has been stored on the membrane 209 after the housing is closed. However, the same or other windows 150 may also allow for visual inspection of color change results of the immunoassay 309 or other test strip. In other configurations, the window(s) 150, if present may only permit visual inspection of some of the media, and not others. That may be useful where the device is used to collect blood samples for compliance with a test such as an FDA 501(k) equivalency test.

Alternatively, the sample could be delivered to an assay region within the housing 101 where capture molecules are exposed to the sample and bind analytes. These analytes could then be bound by a conjugate, making them detectable. The bound analytes may also modify the optical or electrical properties of the surface they are bound to, making them detectable directly.

It can now be appreciated that the action of closing the housing pieces together causes the blood sample to be drawn from the well 104, to be drawn into the capillaries 105 via both capillary action and mechanical force, exiting the capillaries to be deposited onto the sample membrane 209, the immunoassay strip 309, or other media. In particular, the plungers 202 are engaged by housing piece 201-A, and the capillary tubes 105 are in turn held in place within the inlay 252. Thus, as the housing sections are closed together, the plungers 202 are forced into the capillaries 105, which in turn force blood to exit onto the membrane 209.

In some implementations, the material used to fabricate one or more sections or parts of the inlay piece 252 may have an elasticity that is sufficient to hold the capillary tubes 105 in place while the plungers 202 are forced into them. The elasticity of inlay 252 may also be chosen to seal and/or prevent at least some blood from flowing around, rather than flowing through, the capillary tubes 105.

The closed housing 101 also creates a small and isolated internal air space above the sample media. The sample can be further encouraged to dry with the aid of one or more desiccant tablets (not shown) located in this air space. For example, a desiccant may be supported by the backbone 203 adjacent where the sample media 209 sits when the housing is in the closed position.

During or after the housing is closed, a ratcheting mechanism provided by the far end of the backbone 203 encourage the housing to remain shut. For example, the tines 240 may act as a ratcheting pall and engage small holes 245 or other features in the end of housing piece 101-A (See FIG. 1)

when the housing is pushed shut. The tines 240 may be shaped to permit opening of the housing only with a pinching tool that accesses small holes 245 in the side of the housing piece 101-B to release the ratchet pawl, e.g. by pinching the tines 240. Thus, once the device 100 is closed by pushing the housing pieces 101-A, 101-B together, the blood sample remains enclosed within, and ready for transport to a remote lab.

Figure 4A:
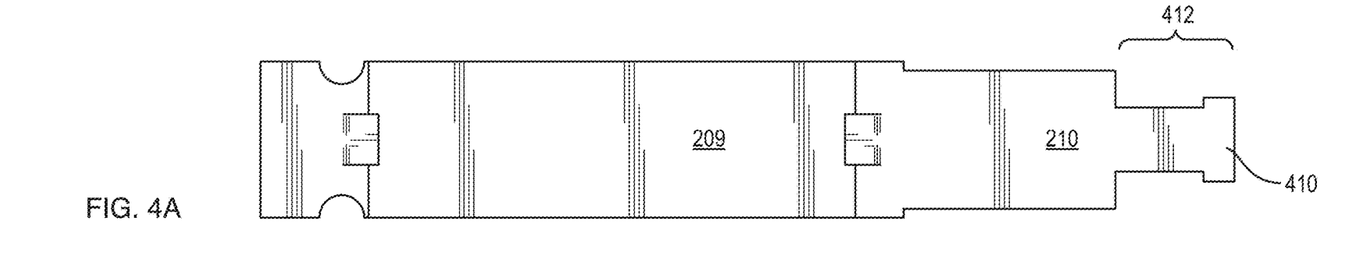
FIGS. 4A and 4B are respective top and side views of one way to implement the media and a media support.
Figure 4B:
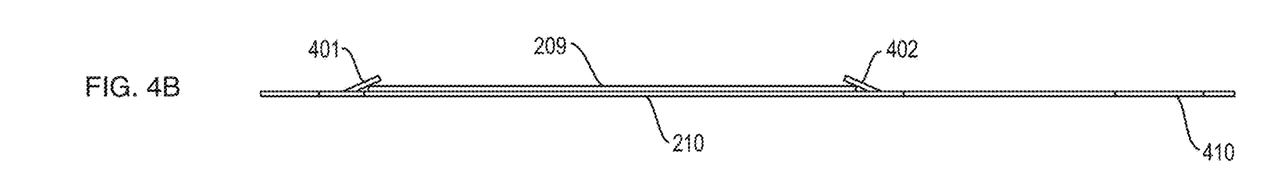
Figure 4C:
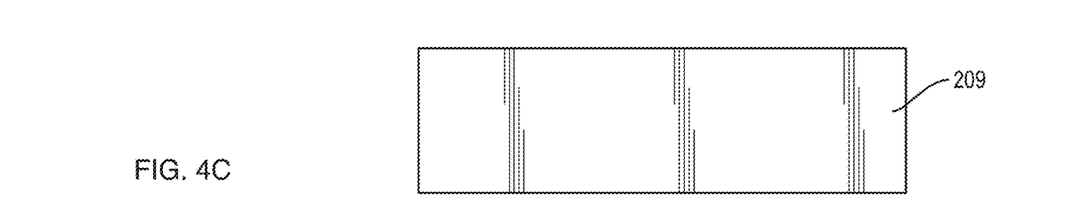
FIG. 4C is a top view of the media and FIG. 4D is a top view of the support.

FIGS. 4A and 4B are respective top and side views of one way to implement the sample media, in this case a membrane 209 and media support 210. FIG. 4C is a top view of the media 209 and FIG. 4D a top view of the support 210.

Figure 4D:
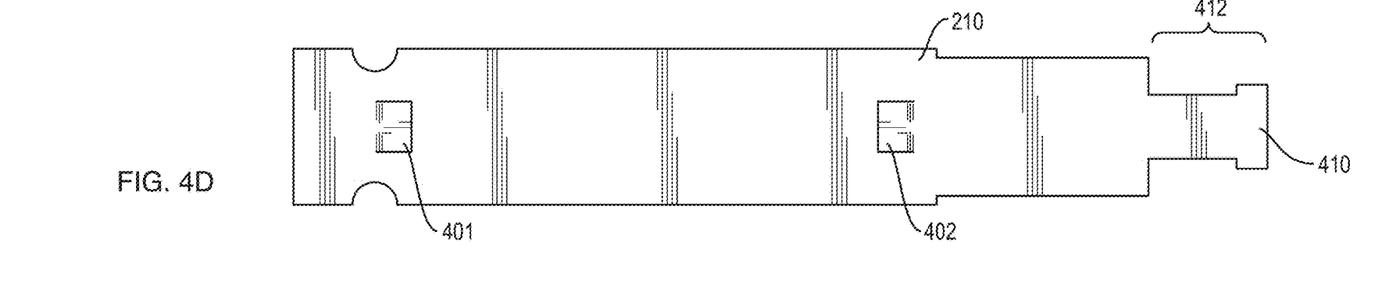

The media 209 may be a generally rectangular, thin, paper or fibrous, membrane that slips under or fits into tabs 401, 402. Tabs 401, 402 may be cut into or formed as port of support 410 to hold media 209 in place. The support 210 may also have a handle portion 410. The handle 410 may conform to extensions 222 in the frame pieces 208, 211. The handle 410 and makes it easier to handle the collection media 209 when it is removed from the housing 101. The handle 410 may also have other features such as shaped peripheral edges 412 to provide a more secure fit of the support 410 (and/or frame pieces 208, 211) within the housing.

Figure 5:
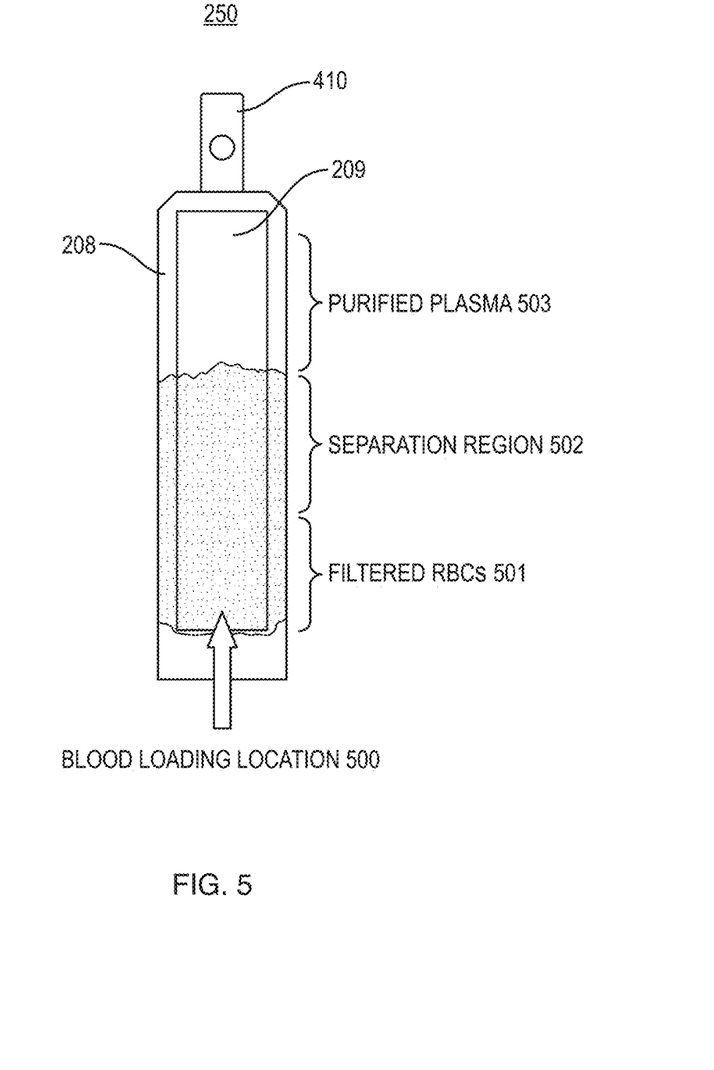
FIG. 5 is a more detailed view of an example media.

FIG. 5 is a plan view of a collection media 250 sometime after a blood sample has been taken and after it has been removed from the housing 101. Note a blood loading location 500 that was located adjacent the sample port 102 when the sample was taken. A first region 501 of the sample media 209 contains filtered red blood cells (RBCs). However other portions of the blood sample have diffused through the media 209, to provide a sample separation region 502 and a purified plasma region 503.

In use, the device 100 is a very convenient way to collect blood expressed by a patient after using a lancet on one of his/her fingers. Commercially-available lancets may be used, and it generally is the choice of the user to select the type of lancet. Once a drop of blood has been expressed on the finger, the patient skims the drop into a well 104 in the sample collection port 102 by gliding the finger across the protruding resilient edge 1030. The blood drop, through gravitational force and surface forces, proceeds to the bottom of the well 104 where it encounters openings in the collection (metering) capillaries 105. From there, blood is further drawn into the collection element 250 including the sample storage media 209, further encouraged by plungers that force blood out of the capillaries as the two housing pieces are closed together.

The closed device 100 then creates a small and isolated internal air space which can be quickly dried with the aid of desiccant tablets contained in an internal pocket. In its current form, use of LF1 paper as a collection media creates spots of red-cell free plasma as well as plasma-depleted whole blood. The LF1 paper's structure causes differential migration, with a slower rate for red cells, resulting in a gradual separation of plasma sample the further down the paper the sample migrates. Plasma is far better for any quantitative blood test, eliminating red cells, which tend to interfere with many analyte assays.

The device 100 therefore offers substantially better opportunity for high-quality quantitative assays as compared to standard dried blood spots. Furthermore, infectious disease tests can still be done on the red cell portion of the dried sample—though plasma-depleted, it is still adequate for accurate detection of infectious agents.

The device is also an ideal mechanism for blood sample preservation and transport. Once the device is closed, the blood sample is enclosed within, largely cut off from the external environment. Upon closing by the user, the device uses the ratcheting mechanism to ensure it remains locked and shut. It can be opened only with the use of a pinching tool that accesses the small holes 245 in the side of the housing 101 to releases the ratchet pawl.

Observations

A. Device that Directs a Fluid Sample to Two or More Media i) It is now understood that a fluid sample collection device may include a housing configurable from an open position to a closed position; a sample collection well for collecting fluid; one or more capillaries or microfluidic channels, arranged to draw in fluid from the sample collection well through capillary action, and having a predetermined volumes, two or more media, arranged to receive fluid dispensed from the capillaries when the housing is moved from the open to the closed position.

ii) The media may include two or more membranes, immunoassay strips, or other substrates. For example, the media may include a collection membrane and an immunoassay strip. The collection membrane(s) and immunoassay strip(s) may be disposed parallel to one another, adjacent an outlet of the capillaries. The collection membrane(s) may receive and store a blood sample for transport, and the immunoassay (or other test) strip(s) may receive and locally process a blood sample within the device.

iii) In some configurations, the sample is delivered to an assay region within the housing where captured blood molecules are exposed to a surface that binds to analytes. These analytes can then be bound by a conjugate to make them detectable by the device.

iv) In another example, one media may be a membrane having an analyte that provides immediate results for a critical condition (such as HIV or hepatitis C), and another membrane may be a collection media, such as LF-1 paper, designed store the blood sample for testing of less critical conditions, at a later time in a lab (such as testing for glucose).

v) A removable support element, may be disposed within the housing, for supporting one or more of the media in place adjacent an exit port of the capillaries.

Therefore, it should be understood that in light of the above, various modifications and additions may be made to the device without departing from the true scope of the inventions made.

The invention claimed is:

1. A biological fluid sample collection device comprising:
a housing comprising a first housing section and a second housing section, the housing configurable from a first position to a second position by moving the first housing section and the second housing section together, the housing enclosing:
a sample collection well;
a capillary in fluid communication with the sample collection well, wherein the capillary is configured to hold a predetermined volume of a sample comprising one or more analytes;
a medium in fluid communication with the capillary, wherein the medium is configured to retain at least a portion of the sample or a derivative thereof, wherein the medium comprises a conjugate configured to bind the one or more analytes to perform a test, wherein the medium comprises an immunoassay strip comprising the conjugate configured to bind the one or more analytes;

a reagent configured to be dispensed onto the medium when the housing is moved from the first position to the second position;

a mechanically actuated fluid controller, configured to cause a predetermined volume of the sample to be dispensed from the capillary onto the medium when the housing is moved from the first position to the second position, wherein the reagent and the sample are mixed when dispensed onto the medium when the housing is moved from the first position to the second position to initiate performance of the test, and wherein, when the housing is in the first position, the sample collection well is positioned on an exterior surface of the housing and is configured to receive the sample from a user and when the housing is in the second position, the sample collection well is fully enclosed within the housing and is inaccessible to the user.

2. The device of claim 1 further comprising:
a support element disposed within the housing and providing support for the medium.

3. The device of claim 1 wherein the mechanically actuated fluid controller comprises:
a plunger, disposed in line with the capillary and configured to dispense fluid from the capillary onto the medium.

4. The device of claim 1 wherein the medium comprises one or more of a paper, fiber, plastic, glass or microfluidic detector.

5. The device of claim 1, wherein the mechanically actuated fluid controller is configured to dispense the predetermined volume of the sample from the capillary onto the medium and the reagent onto the medium in parallel, when the housing is moved from the first position to the second position.

6. The device of claim 1, wherein the housing further comprises a desiccant.

7. A method of performing an assay on a blood sample comprising:
providing a blood sample comprising one or more analytes;
providing a blood sample collection device comprising:
a housing comprising a first housing section and a second housing section, the housing configurable from a first position to a second position by moving the first housing section and the second housing section together, the housing enclosing:
a sample collection well;
a capillary in fluid communication with the sample collection well,
wherein the capillary is configured to hold a predetermined volume of the blood sample
a medium in fluid communication with the capillary, wherein the medium is configured to retain at least a portion of the blood sample or a derivative thereof, wherein the medium comprises a conjugate configured to bind the one or more analytes to perform a test;
a reagent configured to be dispensed onto the medium when the housing is moved from the first position to the second position;
a mechanically actuated fluid controller, configured to dispense a predetermined volume of the blood sample or a derivative thereof from the capillary onto the medium when the housing is moved from the first position to the second position, wherein the reagent and the sample are dispensed onto the medium when the housing is moved from the first position to the second position to initiate performance of the test, and wherein when the housing is in the first position, the sample collection well is positioned on an exterior surface of the housing and is configured to receive the sample from a user, and when the housing is in the second position, the sample collection well is fully enclosed within the housing and is inaccessible to the user;

drawing a portion of the blood sample from the sample collection well into the capillary;

moving the housing from the first position to the second position by pushing the first housing section and the second housing section together, thereby actuating the mechanically actuated fluid controller, dispensing the sample and the reagent onto the medium, and rendering the sample collection well inaccessible to the user;

performing an assay on at least a portion of the blood sample dispensed onto the medium with the conjugate configured to bind the one or more analytes; and indicating the result of the assay on at least a portion of the medium.

8. The method of claim 7 wherein the conjugate configured to bind the one or more analytes is comprised by an immunoassay strip.

9. The method of claim 7 wherein the conjugate configured to bind the one or more analytes is configured to allow for detection of the one or more analytes by (i) modifying an optical property of the medium to make the conjugate detectable by visual inspection, or (ii) modifying an electrical property of the medium to make the conjugate detectable by an electronic circuit.

10. The method of claim 9 further comprising:
providing immediate results of the assay by (i) inducing a color change on the medium, or (ii) inducing an electronic sensor output.

11. The method of claim 7, wherein the device further comprises:
a support element within the housing providing support for the medium.

12. The method of claim 11, wherein the mechanically actuated fluid controller comprises a plunger disposed in line with the capillary, the method further comprising:
operating the plunger, disposed in line with the capillary, to dispense fluid from the capillary onto the medium.

13. The method of claim 7 wherein the medium comprises one or more of a paper, fiber, plastic, glass or microfluidic detector.

14. The method of claim 7, wherein performing the assay further comprises the conjugate configured to bind the one or more analytes binding the one or more analytes, thereby modifying the optical properties of the medium and indicating detection of the one or more analytes via a color change in the medium.

15. The method of claim 7, wherein actuating the mechanically actuated fluid controller by moving the housing from the first position to the second position further comprises dispensing the reagent onto the medium in parallel with dispensing the predetermined volume of the blood sample from the capillary onto the medium.

* * * * *